United States Patent [19]

Wang et al.

[11] 4,029,800

[45] June 14, 1977

[54] NEUROMUSCULAR BLOCKING AGENTS AND ANTAGONISTS

[75] Inventors: Theodore S. T. Wang, Lexington, Mass.; Julius A. Vida, DeWitt, N.Y.

[73] Assignee: Bristol-Myers Company, New York, N.Y.

[22] Filed: May 28, 1976

[21] Appl. No.: 691,154

[52] U.S. Cl. .............................. 424/263; 424/267
[51] Int. Cl.² ................ A61K 31/44; A61K 31/445
[58] Field of Search ........................... 424/263, 267

[56] References Cited

OTHER PUBLICATIONS

Pinson et al., *Archives Internatienales de Pharmcodynomie et de Therapie*, vol. 219, No. 1, Jan. 1976, pp. 52–63.

*Primary Examiner*—Stanley J. Friedman

*Attorney, Agent, or Firm*—Roylance, Abrams, Berdo & Kaul

[57] ABSTRACT

It is disclosed that 2-(4'-pyridyl)-1,3-dioxolane methiodide and 2-(1'-methyl-4'-piperidyl)-1,3-dioxolane hydroiodide are neuromuscular blocking agents or neuromuscular blocking agent antagonists, depending upon the amount of the drug administered.

At doses of $10^{-6}$ to $10^{-4}$ gm./kg. of body weight, they antagonize or reverse the effects of neuromuscular blocking agents, such as d-tubocurarine and succinylcholine, produce post-drug repetitive activity (PDR), block post-tetanic potentiation (PTP), have no direct muscle effect and reverse the PTP suppression caused by d-tubocurarine and succinylcholine; and at doses of $10^{-3}$ to $10^{-2}$ gm./kg. of body weight they act as neuromuscular blocking agents.

6 Claims, No Drawings

NEUROMUSCULAR BLOCKING AGENTS AND ANTAGONISTS

This invention relates to new compounds which act as both neuromuscular blocking agents and as neuromuscular blocking agent antagonists.

Neuromuscular blocking agents are used in five situations: (1) as an adjunct to anesthesia, (2) to prevent fractures during electroshock therapy, (3) in convulsive disorders, (4) to facilitate controlled respiration, and (5) in the diagnosis of myasthenia gravis.

The purpose of anesthesia is not only to render the patient insensible to pain but also, where possible, to facilitate surgery. Normally, the motor nerves carry a constant low level of traffic to the skeletal muscles. These signals induce a contraction of only a small fraction of the muscle fibers at any time, but the activity of these fibers takes up slack so that the muscle is ready for more intense activity at a moment's notice. This background state of slight contraction is called muscle tone. It can be a nuisance during anesthesia when the surgeon must struggle against it to reduce a fracture or when the tone in the flat muscles of the abdomen tends to expel the abdominal contents through an abdominal incision. Before the advent of neuromuscular blocking agents, larger doses of the anesthetic than were required simply to produce unconsciousness had to be administered in order to stop the tonic outflow at the source. General anesthetics, however, have a rather low margin of safety; the concentrations required for muscle relaxation are too close to stage IV of anesthesia. It is, therefore, desirable to use a second agent to abolish muscle tone so that lower concentrations of the general anesthetic can be used. The neuromuscular blocking agents have proved to be a satisfactory class of agents for this role. They abolish tone by blocking the passage of the tonic discharge from the nerve to the muscle. They have subsequently found even wider use during induction of anesthesia, when they are given to relax the laryngeal muscles and thereby facilitate endotracheal intubation.

Depolarizing blocking agents act by prolonging the depolarization of the postjunctional membrane, thus mimicking the effects of acetylcholine. Because the membrane is still in a refractory period when the next nerve impulse reaches it, there can be no muscular contraction.

Succinylcholine (0.5 to 1.9 gm./kg.) is the agent of choice when the neuromuscular block is required solely to aid endotracheal intubation since the rapid onset (20 to 40 sec.) and short duration of action (2 to 5 min.) facilitates early intubation and prompt return of spontaneous respiration. Comparable relaxation with tubocurarine would require such a large dose that some effects would persist for 20 to 30 min. or more.

The main drawback of succinylcholine is the initial fasciculation seen as it depolarizes the muscle fibers. Thus, it is referred to as a depolarizing blocking agent. Since the patient is anesthetized, there is no discomfort at the time, but he may feel stiff or complain of pain the next day, especially if the procedure was a minor one enabling early ambulation. Fasciculation can be ameliorated by a second agent, e.g., by a small dose of tubocurarine.

For procedures requiring prolonged muscle relaxation, several methods are available. Those most frequently used are a continuous intravenous infusion of 0.1 to 0.2 % succinylcholine or intermittent doses of tubocurarine or gallamine. The choice depends on the type of general anesthetic used, the condition of the patient, and the type of surgery contemplated.

Succinylcholine may produce tachyphylaxis, apnea and cardiac arrest in patients with burns, massive trauma or neuromuscular disease. Succinylcholine may stimulate the sympathetic neurons system and thereby cause an increase in blood pressure.

Another type of blocking agent, classified as competitive or nondepolarizing blocking agents, combine with the cholinergic receptors and this prevents acetylcholine from reaching these sites. They block depolarization of the postjunctional membrane and prevent transmission of the motor nerve impulse. Characteristics of a nondepolarizing block include absence of fasciculations, "fade" response of the muscle fibers after tetanic stimulation and post-tetanic facilitation. Some of these drugs are discussed below:

Curare and D-Tubocurarine

The onset of these drugs occurs almost immediately after a single intraveneous injection. The effect decreases within 10 minutes as the drug moves from the plasma into the tissues. Muscular strength becomes completely normal after 40 minutes. Other actions of d-tubocurarine include release of histamine and blockade of sympathetic ganglia, leading to hypotension. Eighty-five percent of the total dose is excreted unchanged in urine or eliminated in the bile. The average dose is 6 to 9 mg. for a single injection and 3 to 5 mg. for repeated administration. The effect of curare is intensified by the concomitant use of neomycin or ether. The dose of curare should therefore be modified accordingly.

Gallamine (Flaxedil)

The duration of action of galamine is shorter than that of curare, and the drug is excreted unchanged in the urine. Gallamine also acts to block the parasympathetic ganglia, producing tachycardia. The average intravenous dose is 1.0 mg./kg.

Pancuronium (Pavulon)

Pancuronium, a recently marketed agent, is a steroid bisquaternary ammonium compound with five times the therapeutic potency of d-tubocurarine. Unlike d-tubocurarine, pancuronium lacks histamine release activity and has a weak ganglion blocking effect. Pancuronium is given intravenously at a dosage range of 0.04 to 0.10 mg./kg. Onset of action occurs within 1 minute after a single injection. The duration of action is three to five times longer than d-tubocurarine.

Ideally, one would like to produce a neuromuscular block which is immediate in onset, which is of exactly the right intensity, and which disappears immediately when no longer needed. In practice, the first of these requirements is approximated fairly well. The second and particularly the third are harder to achieve. At the end of the operation, a considerable degree of block may persist either because of an overdosage (for example, because of greater than normal sensitivity of the patient), because of accumulation with repeated administration during a long procedure, or simply because the normal rate of elimination is not very rapid. In such cases, it would be very useful to have an agent which would abolish the action of the neuromuscular blocking agent, i.e., a neuromuscular blocking agent antagonist, thereby assuring the return of neuromuscular transmission and, in particular, the resumption of normal respiration.

More especially, there is a continual need in neuromuscular pharmacology for drugs that reverse d-tubocurarine and succinylcholine blockade. Numerous agents, e.g., neostigmine, edrophonium and pyridostigmine, reverse d-tubocurarine blockade but either have no effect on or potentiate succinylcholine.

It is an object of this invention to find new neuromuscular blocking agents.

It is another object of this invention to find new neuromuscular blocking agent antagonists, especially ones which will reverse succinylcholine blockade.

These and other objects are achieved by the practice of this invention which, briefly, comprises administering to a host animal, including man, either 2-(4'-pyridyl)-1,3-di-oxolane methiodide, hereinafter referred to as KCL-301-14, and 2-(1'-methyl-4'-piperidyl)-1,3-dioxane hydroiodide, hereinafter referred to as KCL-301-39. These compounds are administered parenterally, i.e., intravenously, intramuscularly or subcutaneously. At doses of $10^{-6}$ to $10^{-4}$ gm./kg. of body weight they antagonize or reverse the effects of neuromuscular blocking agents, such as d-tubocurarine and succinylcholine, produce postdrug repetitive activity (PDR), block post-tetanic potentiation (PTP), have no direct muscle affect and reverse the PTP suppression caused by d-tubocurarine and succinylcholine; and at doses of $10^{-3}$ to $10^{-2}$ g/kg of body weight they act as neuromuscular blocking agents.

KCL-301-14 and KCL-301-39 were prepared by the following reaction sequences:

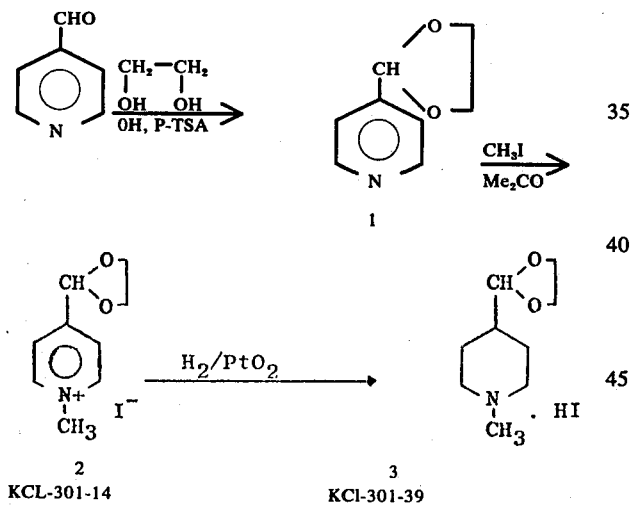

EXPERIMENT 1

2-(4'-pyridyl)-1,3-dioxolane (1)

A mixture of pyridine-4-carboxaldehyde (10.7 g., 0.1 mole), ethylene glycol (18.6 g., 0.3 mole) and p-toluenesulfonic acid (19 g., 0.11 mole) in benzene (200 ml.) was azeotropically distilled using a Stark-Dean collector for 16 hours, during which time 2 ml. of water was collected. The mixture was then cooled to 25° C. and 10% sodium bicarbonate was added to pH 7.5. After the benzene layer was separated, the water layer was extracted twice, first with benzene (50 ml.) and then with ether (50 ml.). The extracts were combined and the solvent was evaporated. Compound 1, a viscous liquid (9.4 g., 62%), was collected at 86°–8° C./1mm. The hydrochloride salt of compound 1 was prepared by dissolving compound 1 in a small amount of ether and passing HCl through the solution. The precipitate was collected and crystallized from ethanol. Obtained was the hydrochloride salt of compound 1, mp. 173°–174° C.

EXPERIMENT 2

2-(4'-pyridyl)-1,3-dioxolane methiodide (2)

To a solution of 1 (15.1 g., 0.1 mole) in acetone (100 ml.) was added dropwise methyl iodide (17.6 g., 0.125 mole) and the mixture was heated at reflux for 6 hours. Crystalls appeared which were filtered and washed with acetone and ether. Obtained was compound 2, (21.1 g., 94%), mp. 161°–162° C.; tlc (CHCl$_3$-Me$_2$CO, 9:1).

EXPERIMENT 3

2-(1'-methyl-4'-piperidyl)-1,3-dioxolane hydroiodide (3)

To a solution of 2 (29.31 g., 0.1 mole) in methanol (150 ml.) was added PtO$_2$ (880 mg.). The mixture was hydrogenated at 25° C. at an initial H$_2$ pressure of 60 lb./in.$^2$. When hydrogenation was complete (about 3 hours), the catalyst was filtered, the solvent was evaporated, and the residue was crystallized from Me$_2$CO and recrystallized from EtOH to give 3, (26.7 g., 88%) mp. 116°–117°; tlc (CHCl$_3$-Me$_2$CO, 9:1).

ANALYTICAL DATA

| Cmpd. No. | Formula | %C Calc'd | %C Found | %H Cald'd | %H Found | %N Calc'd | %N Found | %Cl Cald'd | %Cl Found | %I Calc'd | %I Found |
|---|---|---|---|---|---|---|---|---|---|---|---|
| 1 | C$_8$H$_{10}$NO$_2$Cl | 51.21 | 51.29 | 5.36 | 5.50 | 7.46 | 7.41 | 19.43 | 19.51 | — | — |
| 2 | C$_9$H$_{12}$NO$_2$I | 36.88 | 36.80 | 4.12 | 4.05 | 4.78 | 4.69 | — | — | 43.26 | 43. |
| 3 | C$_9$H$_{18}$NO$_2$I | 36.14 | 36.10 | 6.06 | 6.07 | 4.69 | 4.62 | — | — | 42.55 | 42. |

The dioxolane derivative (1) was prepared by azeotropic distillation of pyridine-4-carboxaldehyde with ethylene glycol in the presence of p-toluenesulfonic acid. The methiodide salt (2) was formed in quantitative yield by treating 1 with methyl iodide in acetone. Catalytic hydrogenation of 2 using PtO$_2$ furnished 2-(1'-methyl-4'-piperidyl)-1,3-dioxolane hydroiodide (3). The following experiments illustrate these reactions:

The preparation of these compounds is also described in a thesis by T. Wang entitled "The Synthesis of Succinylcholine and Azepinoindole Compounds Structurally Related to Iboga" (University of Maryland, College Park), University Microfilms (Ann Arbor, Mich.), Order No. 65–990, (1965).

KCL-301-14 and KCL-301-39 are particularly useful in reversing succinylcholine blockage since there is no commercially available drug which is able to accomplish this effect. Succinylcholine blockage may be induced by any halogen derivative of succinylcholine, e.g., succinylcholine bromide, succinylcholine chloride or succinylcholine iodide.

The effects of these compounds on neuromuscular transmission were evaluated on in vivo cat soleus preparations as follows:

EXAMPLE 1

Adult cats weighing 2-3 kg. were anesthetized with 70 mg. alpha chloralose per kg. intravenously (i.v.). The two heads of the gastrocnemius muscle were removed and the soleus nerve and muscle isolated. The exposed tissues were covered with mineral oil pools thermoregulated at 37° C. The calcaneous bone was cut and attached to a Grass FT-10 force transducer through a steel rod. Contractile activity was recorded continuously on a polygraph. Supramaximal stimuli consisting of rectangular pulses of 0.1 msec duration were applied to the soleus nerve by means of bipolar platinum-irridium electrodes. These stimuli were delivered at a frequency of 0.4 Hz. and every 5 minutes a high frequency (499 Hz.) stimulus train was interposed for a period of 10 seconds. This produced a tetanic contraction of the muscle which was followed by posttetanic potentiation (PTP) of the contraction.

In some animals, a dorsal laminectomy was performed on vertebrae $L_5$-$S_1$. Filaments containing single axons from decentralized ventral roots were placed on bipolar platinum-irridium recording electrodes. These recorded antidromically conducted action potentials which were stored on magnetic tape for analysis and photography. Details of the method appear in reports by Standaert, J. Gen. Physiol., 47:53 (1963), and J. Gen. Physiol., 47:987 (1964), the disclosures of which are incorporated herein by reference.

In another series of animals, the effects of the agents were evaluated by stimulating the muscle directly in the presence of enough d-tubocurarine to block neuromuscular transmission.

KCL-301-14 and KCL-301-39 were dissolved in 0.85 % saline solution and administered intra-arterially (i.a.) in a volume of 0.1 ml. per kg.

Changes in contraction strength are expressed as percent change from predrug values. PTP changes are expressed as the alteration of the net potentiation of the peak response. That is, the mean control tension was subtracted from the peak PTP response to yield a net PTP, and the drug-induced change in the latter was determined.

Inter-arterial injections of both KCL-301-14 and KCL-301-39 in concentrations ranging from $10^{-6}$ to $10^{-4}$ gm./kg. increased the force of contraction of the soleus muscle to approximately 250% of control. Contracture of the muscle also occurred during the period of potentiation. Multiple action potentials in the ventral root occurred concomitantly with the increase in contraction strength. This is referred to as post-drug repetitive activity (PDR). The increased contraction and PDR lasted for about 2 to 3 minutes and were followed by a return to control.

In higher concentrations ($10^{-3}$ gm./kg. or greater) both agents produced a blockade rather than a potentiation of the muscle contraction. The blockade was quite prolonged taking up to 2 hours to return to control levels. Both chemicals, in concentrations ranging from $10^{-4}$ to $10^{-3}$ gm./kg., produced a progressive decline in PTP. The PTP suppression lasted for 20 minutes with concentrations of the drug which did not block the muscle contraction. PTP suppression lasted for up to 3 hours after concentrations which decreased the muscle contraction.

Both agents, in concentrations up to $10^{-1}$ gm./kg. had no effect on the directly stimulated muscle.

The two drugs, in concentrations of $10^{-5}$ and $10^{-4}$ gm./kg. reversed the neuromuscular blockade produced by the non-depolarizing agents, d-tubocurarine, gallamine and pancuronium. In addition, both agents also reversed blockade produced by the depolarizing agent succinylcholine. The agents also reversed the PTP suppression by d-tubocurarine and succinylcholine. The blockade agents were administered in doses sufficient to give 50% muscle paralysis.

When injected intravenously in concentrations up to $10^{-1}$ gm./kg. neither drugs produced an alteration in either the heart rate or blood pressure.

From the results of this invention, KCL-301-14 appears to have some effects like those of the anticholinesterase agents and some effects which are different. In low doses the agent increased the force of contraction of the cat soleus muscle by causing the nerve terminal to fire repetitively in response to a single stimulus. In higher doses, the agent depresses neuromuscular transmission with little or no initial facilitation. The drug also depresses PTP over a wide range of concentrations, an indication of a depressant action on the nerve terminal. In addition, KCL-301-14 reverses the neuromuscular blockade produced by the anticholinesterase agents. However, in contrast to the anticholinesterase agents, the drug reversed neuromuscular blockade produced by the depolarizing drug, succinylcholine.

KCL-301-39 has the same effects in the same dosages as KCL-301-14.

In summary, in the cat, both KCL-301-14 and KCL-301-39 had a stimulatory and a depressant effect on the motor nerve terminal and both drugs were able to reverse the blockade of depolarizing and non-depolarizing agents.

EXAMPLE 2

The force of contraction of the soleus muscle produced by stimulation of the sciatic nerve was recorded in a conventional manner. The test compounds as well as standard myoneural blocking agents were injected into the artery leading to the muscle.

Concentrations of $10^{-5}$ to $10^{-4}$ gm./kg. of both compounds increased the contraction strength. This action was quite persistent, in some muscles lasting for 10 to 15 minutes. Concentrations of $10^{-3}$ and $10^{-2}$ gm./kg. produced an immediate decrease in the twitch strength that lasted between 40 and 60 minutes. Myoneural blockade produced by either agent could be partially reversed by applying a tetanic stimulus of 400 Hz. to the nerve, on the other hand, blockade was enhanced by the anticholinesterase agent edrophonium. The former action is typical of nondepolarizing blockers such as d-tubocurarine while the latter action is typical of the depolarizing blockers such as succinylcholine. Thus, it appears that the mechanisms of blockade of the experimental compounds is different than that of pure depolarizing or non-depolarizing compounds.

Both compounds in concentrations of $10^{-4}$ gm./kg. reversed blockade produced by various non-polarizing neuromuscular blocking agents such as d-turbocurarine and gallamine as well as by the depolarizing blocker succinylcholine. These blocking agents had been administered in doses sufficient to cause 50% muscle blockade. WE CLAIM:

1. A process for causing neuromuscular blockage or for antagonizing the effects of a neuromuscular blocking agent which comprises parenterally administering to a host animal a compound selected from the group consisting of 2-(4'-pyridyl)-1,3-dioxolane methiodide and 2-(1'-methyl-4-piperidyl)-1,3-dioxolane hydroiodide.

2. A process according to claim 1 wherein said compound is administered at a dose of $10^{-6}$ to $10^{-4}$ gm./kg. of body weight to antagonize the effects of a previously administered neuromuscular blocking agent.

3. A process according to claim 2 wherein said previously administered neuromuscular blocking agent is succinyl-choline chloride.

4. A process according to claim 1 wherein said compound is administered at a dose of $10^{-3}$ to $10^{-2}$ gm./kg. of body weight to cause neuromuscular blockage.

5. A process according to claim 1 wherein said compound is 2-(4'-pyridyl)-1,3-dioxolane methiodide.

6. A process according to claim 1 wherein said compound is 2-(1'-methyl-4-piperidyl)-1,3-dioxolane hydroiodide.

* * * * *